(12) United States Patent  
Abt

(10) Patent No.: US 10,201,270 B2  
(45) Date of Patent: Feb. 12, 2019

(54) OPHTHALMIC SURGICAL IMAGE PROCESSING

(71) Applicant: Novartis AG, Basel (CH)

(72) Inventor: Niels A. Abt, Schaffhausen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/118,070

(22) PCT Filed: Oct. 16, 2015

(86) PCT No.: PCT/EP2015/074032  
§ 371 (c)(1),  
(2) Date: Aug. 10, 2016

(87) PCT Pub. No.: WO2017/063714  
PCT Pub. Date: Apr. 20, 2017

(65) Prior Publication Data  
US 2018/0214019 A1    Aug. 2, 2018

(51) Int. Cl.  
*G06K 9/00* (2006.01)  
*A61B 3/00* (2006.01)  
*A61B 3/12* (2006.01)  
*A61B 3/13* (2006.01)  
*A61B 3/14* (2006.01)  
*A61F 9/007* (2006.01)  
*A61F 9/008* (2006.01)

(52) U.S. Cl.  
CPC .......... *A61B 3/0025* (2013.01); *A61B 3/0041* (2013.01); *A61B 3/12* (2013.01); *A61B 3/13* (2013.01); *A61B 3/14* (2013.01); *A61F 9/007* (2013.01); *A61B 2576/00* (2013.01); *A61F 2009/00844* (2013.01)

(58) Field of Classification Search  
CPC ....... A61B 3/0025; A61B 3/0041; A61B 3/13; A61B 2576/00; A61B 3/14; A61F 2009/00844; A61F 9/007  
See application file for complete search history.

(56) References Cited

U.S. PATENT DOCUMENTS

| | | | | |
|---|---|---|---|---|
| 5,693,013 A | * | 12/1997 | Geuder | ............... A61F 9/00736 604/35 |
| 6,338,559 B1 | * | 1/2002 | Williams | ............. A61B 3/1015 351/212 |
| 2002/0047992 A1 | * | 4/2002 | Graves | .................. G02B 26/06 351/212 |

(Continued)

FOREIGN PATENT DOCUMENTS

| | | |
|---|---|---|
| EP | 2645701 A1 | 10/2013 |
| EP | 2806402 A1 | 11/2014 |
| WO | 2014/074595 A1 | 5/2014 |

*Primary Examiner* — Amir Alavi

(57) ABSTRACT

A system and method for ophthalmic surgery in which a portion of the light reflected by the eye passes through a lens that inverts the image and a portion of the light reflected by the eye does not pass through the lens. A digital image of both light that passed through the lens (lens image) and light that has not (peripheral image) is created using an image sensor. A processing resource identifies the boundary between the lens image and peripheral image and inverts at least a portion of either the lens image or the peripheral image to produce a corrected image in which no or only a small portion of the image is inverted as compared to the eye.

18 Claims, 4 Drawing Sheets

(56) References Cited

U.S. PATENT DOCUMENTS

| | | | |
|---|---|---|---|
| 2011/0028951 A1* | 2/2011 | Raksi | A61F 9/008 606/4 |
| 2012/0098926 A1 | 4/2012 | Kweon | |
| 2017/0086667 A1* | 3/2017 | Zhou | A61B 3/1015 |
| 2018/0017739 A1* | 1/2018 | Diao | G02B 6/3861 |
| 2018/0192871 A1* | 7/2018 | Abt | A61B 3/13 |
| 2018/0214019 A1* | 8/2018 | Abt | A61B 3/0025 |

* cited by examiner

OPHTHALMIC SURGICAL IMAGE PROCESSING

CROSS REFERENCE TO RELATED APPLICATIONS

This application is a section 371 national stage phase of International Application No. PCT/EP2015/074032, filed 16 Oct. 2015, titled "OPHTHALMIC SURGICAL IMAGE PROCESSING," which is hereby incorporated by reference in its entirety.

TECHNICAL FIELD

The present disclosure relates to ophthalmic surgery, and more specifically, to systems for and methods of processing an image received from a system containing at least one lens that inverts a portion of the image.

BACKGROUND

Ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

One type of ophthalmic surgery, vitreoretinal surgery, encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced into the surgical field to perform any of a variety of different procedures (FIG. 1A). The surgical microscope provides imaging and optionally illumination of the fundus during vitreoretinal surgery. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus. For many types of vitreoretinal surgery using the surgical microscope, the surgeon may desire to have a very wide field of view of the fundus that extends beyond the equator and even out to the ora serrata.

Many such systems use a primary lens, such as an indirect lens, that inverts a portion of the image of the surgical field seen by the surgeon. Absent further correction, this type of system provides the surgeon an inverted view of the ends of the instruments in the surgical field (FIG. 1B). The surgeon must mentally correct the view in order to move the instruments properly. Such mental corrections are difficult to perform and negatively impact surgical outcomes in many instances. To render the situation even more difficult, most systems also provide the surgeon with a view of an area of the eye outside of the indirect lens field. In this area, the bodies of the surgical instruments are oriented correctly (FIG. 1B).

To at least render the ends of the surgical instruments as they are actually positioned, many systems, such as stereo digital inverters, contain an inverter lens or perform digital image processing that further inverts the image of the surgical field. This results in the ends of the surgical instruments being portrayed accurately within the surgical field, but portions of the image that were not previously inverted then become inverted, again resulting in a disconnect between the bodies of the surgical instruments in part of the surgical field, and the ends of the instruments. The resulting image (FIG. 1C), as compared to the actual location of the instruments (FIG. 1A), can be seen by comparing FIG. 1A and FIG. 1C. Although this type of image requires less mental correction by the surgeon, the inverted portrayal of part of the bodies of the instruments is distracting and requires mental correction. As a result, surgical outcomes are still negatively impacted in many instances.

SUMMARY

The present disclosure provides a system for performing ophthalmic surgery. The system includes a primary lens through which light reflected from an eye undergoing ophthalmic surgery passes. The system also includes an image sensor that converts the light passed through the primary lens into a lens image and light that has not passed through the primary lens into a peripheral image. The lens image and the peripheral image form a digital image. The system further includes a processing resource that identifies a boundary between the lens image and the peripheral image in the digital image and inverts at least a portion of the lens image or at least a portion of the peripheral image to form a corrected image. In addition, the system includes a display that displays the corrected image.

In additional embodiments, which may be combined with the system above and with one another unless clearly mutually exclusive, no portion of the corrected image is inverted as compared to the eye or less than 10% of the corrected image is inverted as compared to the eye. There may be at least one surgical instrument in the eye undergoing ophthalmic surgery and no portion of the corrected image containing a surgical instrument is inverted as compared to the surgical instrument or less than 10% of the corrected image is inverted as compared to the surgical instrument. The lens may contain an identifier that is detected by the processing resource to identify the boundary. The processing resource may use huge circle detection to identify the boundary. The processing resource may use continuity detection to identify the boundary.

The present disclosure further provides a method of performing ophthalmic surgery by placing a primary lens between the eye and an image sensor such that the image sensor receives light reflected from the eye that passes through the lens and light reflected from the eye that does not pass through the lens, converting the light received by the image sensor to a digital image containing a lens image converted from light that passes through the lens and a peripheral image converted from light that does not pass through the lens, identifying a boundary between the lens image and the peripheral image using a processing resource, inverting at least a portion of the lens image or at least a portion of the peripheral image to form a corrected image, and displaying the corrected image.

In additional embodiments, which may be combined with the system above and with one another unless clearly mutually exclusive no portion of the corrected image is inverted as compared to the eye, or less than 10% of the corrected image is inverted as compared to the eye. At least one surgical instrument may be inserted into the eye and no portion of the corrected image containing a surgical instrument is inverted as compared to the surgical instrument, or less than 10% of the corrected image is inverted as compared to the surgical instrument. The primary lens may contain an identifier and the method may include detecting the identifier and identifying the boundary using the identifier. The identifier may be located around the periphery of the lens, such that it corresponds with the boundary. The processing resource may use the identifier to obtain information regarding the dimensions of the lens from a database and may use the information regarding the dimensions to identify the boundary. Identifying the boundary may include the processing resource using huge circle detection. A dye may be introduced into the eye and color may be used in huge circle detection to identify the boundary and exclude non-lens circular or elliptical features. Identifying the boundary may include the processing resource using continuity detection. The processing resource may use two or more of an identifier located on the primary lens, huge circle detection, or continuity detection to identify the boundary.

The above systems and methods may further be used in combination with one another and with additional features described herein.

BRIEF DESCRIPTION OF THE DRAWINGS

For a more complete understanding of the present invention and its features and advantages, reference is now made to the following description, taken in conjunction with the accompanying drawings, in which.

DETAILED DESCRIPTION

The present disclosure relates to ophthalmic surgery, and more specifically, to systems for and methods of processing an image received from a system containing at least one lens that inverts a portion of the image to detect inverted portions of the image and reinvert only these portions to produce a final image without any inversions. Such an image more accurately portrays the surgical field, does not require mental correction of the surgical instrument positions by the surgeon, and decreases the difficulty of ophthalmic surgery, which may improve surgical outcomes for patients.

Figure 1A:
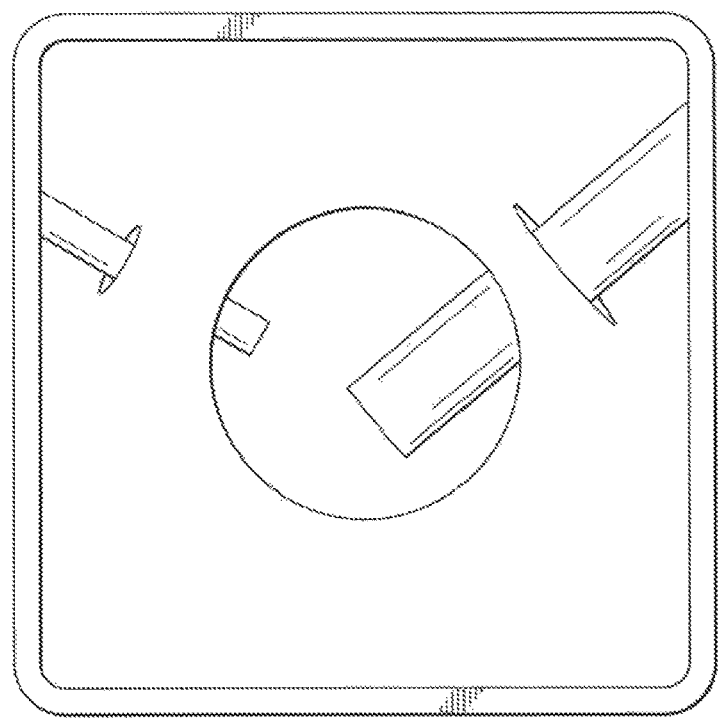
FIG. 1A is an image of the surgical field during an ophthalmic surgery, as known in the prior art.
Figure 1B:
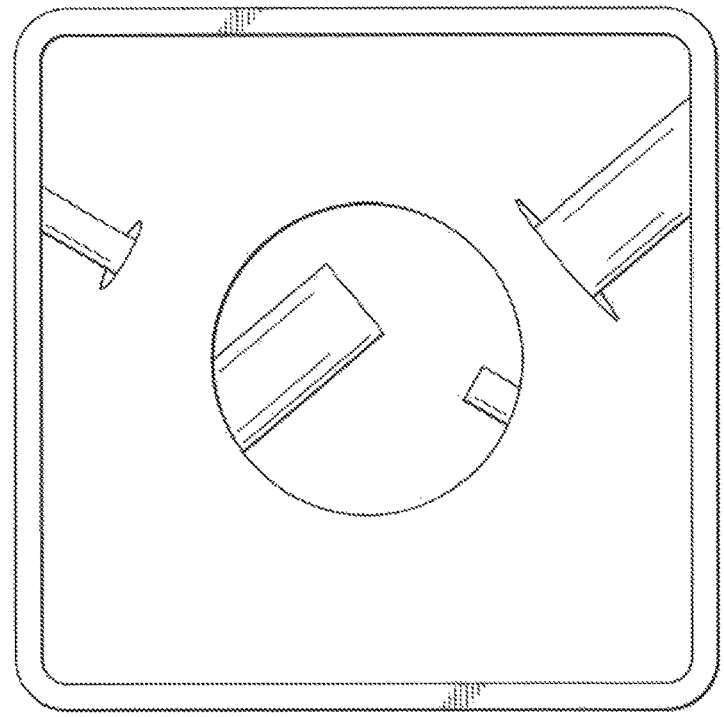
FIG. 1B is an image portraying the surgical field during an ophthalmic surgery in which a portion of the image that passes through a primary lens is inverted.
Figure 1C:
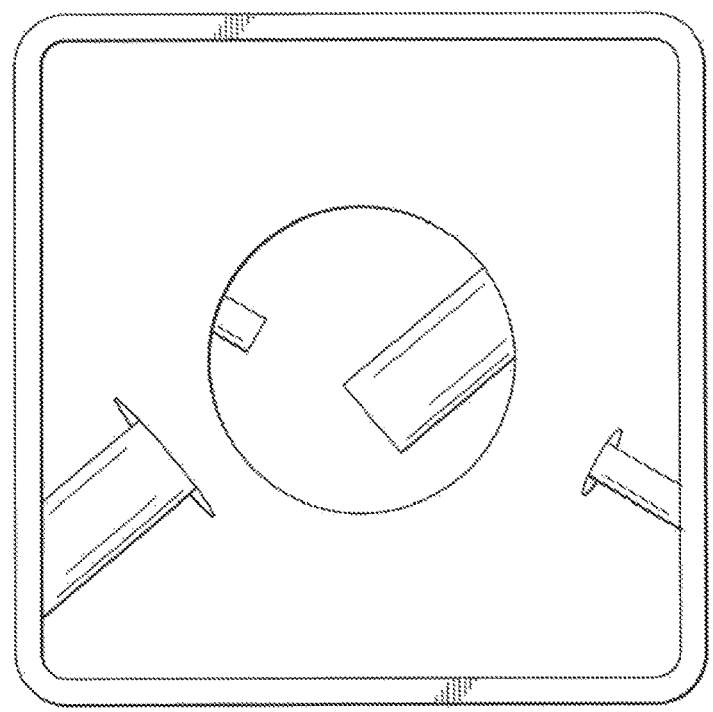
FIG. 1C is an image portraying the surgical field during an ophthalmic surgery in which a portion of the image that does not pass through a primary lens is inverted.
Figure 2:
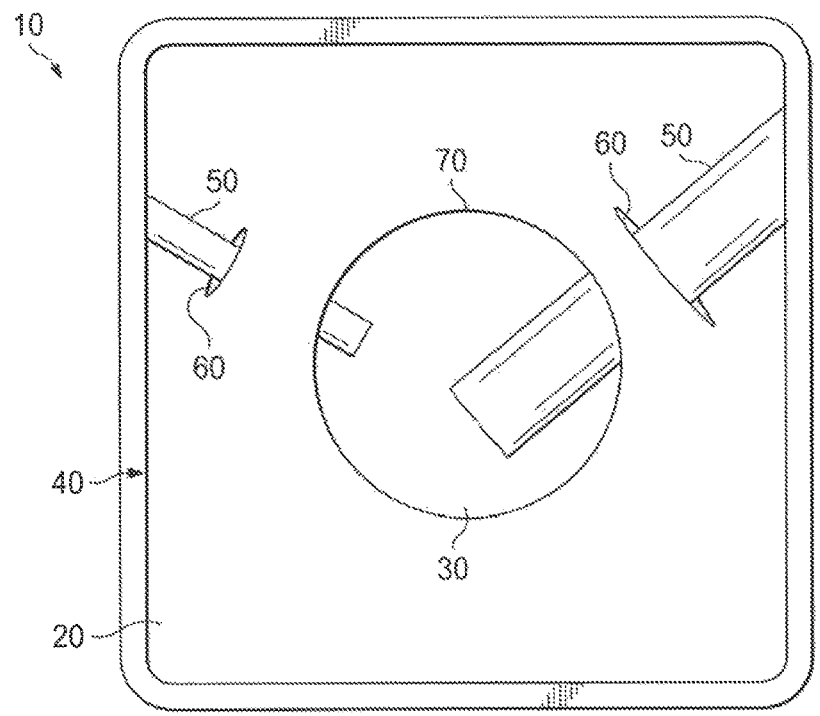
FIG. 2 is a digitally processed image portraying the surgical field during an ophthalmic surgery in which the image contains components that pass through a primary lens and portions that do not, but no portion of the image is inverted.

Referring now to the drawings, FIG. 2 presents a corrected image 10 of the surgical field during an ophthalmic surgery on eye 20. The image contains a lens image 30, which has passed through and been inverted by a primary lens, as well as a peripheral image 40, which has not passed through a primary lens. Surgical instruments 50 passing into eye 20 at insertion points 60 are visible in corrected image 10. Due to differences in magnification of lens image 30 and peripheral image 40, a lens boundary 70 may also be visible. FIG. 2 depicts a surgical field as shown in FIG. 1A. In FIG. 2, no portion of corrected image 10 is inverted. Alternatively, there may be no portion of corrected image 10 containing an instrument 50 is inverted. Further alternatively, less than 10% of corrected image 10 may be inverted; or less than 10% of the total portion of corrected image 10 containing an instrument 50 may be inverted. Although an image with no inversion may be easier to produce or better suited to reducing surgical errors, an image containing small inversions, particularly if these inversions do not include the surgical instruments or other visually distinguishable features may also be acceptable. This is especially true if these inversions do not require mental correction by the surgeon in order to perform the surgery or if tolerating these inversions provides advantages in quicker image processing, more accurate processing of portions of the image with distinguishable features, or image processing using simpler, more reliable, or cheaper equipment. For instance, portions of the image near lens boundary 70 may remain inverted without harm if they are too blurry or dark to provide useful information to the surgeon.

All or a part of corrected image 10 may be magnified. Typically lens image 30 is magnified between 5× and 40×, more particularly between 5× and 15×. Only lens image 30 may have been passed through a lens, all of corrected image 10 may have been passed through a lens, or portions of image 10 may have been passed through one or more lenses.

Figure 3:
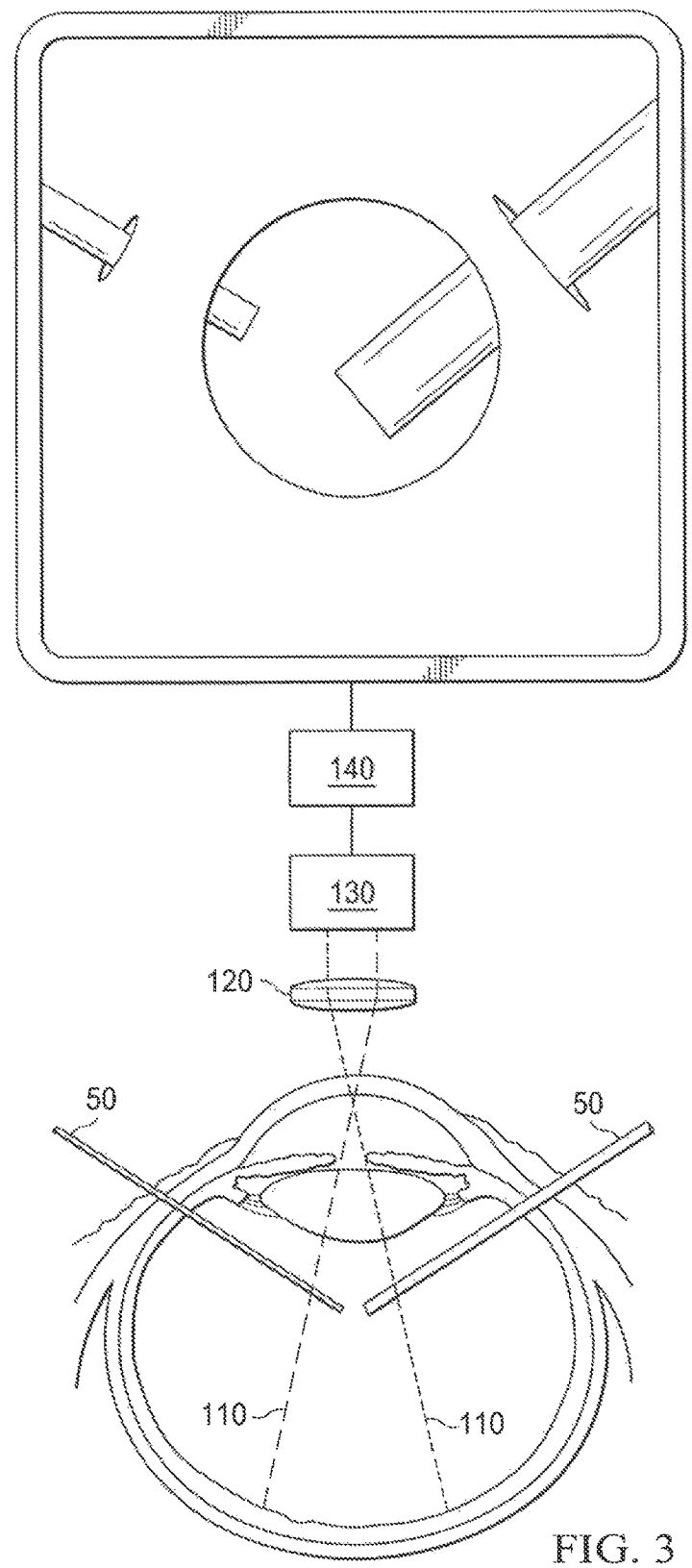
FIG. 3 is a system for acquiring, digitally processing, and displaying an image of the surgical field in an ophthalmic surgery in which no portion is inverted.

FIG. 3 presents an ophthalmic surgery system 100 for performing surgery on an eye 20 using surgical instruments 50. Reflected light beams 110 (shown as two representative beams only) pass out of eye 20 through primary lens 120 and are inverted by lens 120 in the process. Image sensor 130 intercepts light beams 110 as well as other light that has not passed through lens 130. Light beams 110 that have passed through lens 130 form lens image 30, while light that has not passed through lens 130 forms peripheral image 40. Image sensor 130 forms a digital image using this light to portray the surgical field of eye 20. Processing resource 140 detects the boundary of lens 120 and inverts the portion of the image found within this boundary. Finally, display 150 displays corrected image 10.

Although FIG. 3 depicts a system with only one lens 120 because such a system may be more reliable and cheaper to manufacture and maintain, systems with more than one lens are also possible. For instance, a system may contain a primary lens 120 and a second, inverter lens that inverts all of light before it reaches image sensor 130. In such a system, after the digital image is formed and the boundary of lens 120 is detected, the portion of the image found outside of the boundary is inverted.

Instruments 50 include any ophthalmic surgical instruments, particularly those used in vitreoretinal surgeries. Such instruments include cannulas, light probes, vitrectomy probes, forceps, scissors, laser probes, pics, and spatulas.

Primary lens 120 may include any magnifying lens suitable for use in ophthalmic surgery, including direct and indirect contact lenses. System 100 may further contain instruments to position and focus lens 120. System 100 may also contain additional lenses to be used in conjunction with primary lens 120, or in place of primary lens 120. For instance, system 100 may include a wide-view lens that may be switched with primary lens 120. Lenses may be direct contact lenses or indirect lenses, as needed.

Image sensor 130 may be any electronic device able to convert light to a digital image. For instance, it may be a digital camera, a light-to-digital sensor, a semiconductor charge-coupled device (CCD), a complementary metal-oxide-semiconductor (CMOS) device, an N-type metal-oxide-semiconductor (NMOS) device, or another electronic device containing an array of photodiodes as part of one or more integrated circuits. Image sensor 140 may contain additional lenses or other elements to assist with image capture. Image sensor 130 produces a digital image with sufficient resolution to produce a usable corrected image 10, even after image processing.

Processing resource 140 may include any physical device able to store and run algorithms as described herein in order to produce corrected image 10. Although processing resource 140 is depicted separately form image sensor 130 in FIG. 3, they may be part of a single physical device, such as a single computer or set of integrated circuits.

Display 150 may include any type of screen or projector able to display corrected image 10 with sufficient resolution to be usable in an ophthalmic surgery. For instance, it may include any type of screen or projector used in connection with ophthalmic surgery, including displays of the type used in conventional vitreoretinal surgical systems that present digital images. In most instances, a special type of display for corrected image 10 as compared to other digital images used in ophthalmic surgery is not needed. Display 150 may display a single image as shown, or two images for stereoscopic viewing. Although display 150 is depicted separately from processing resource 140 and image sensor 130, it may be part of a single physical device, such as a single computer or set of integrated circuits, with processing resource 140, image sensor 130, or both.

System 100 may further contain other elements to facilitate its uses, such as memory to store corrected image 10 or instructions for processing resource 140, electrical connections, and hardware to position and focus any lenses, such as lens 120, and to position image sensor 130.

Figure 4A:
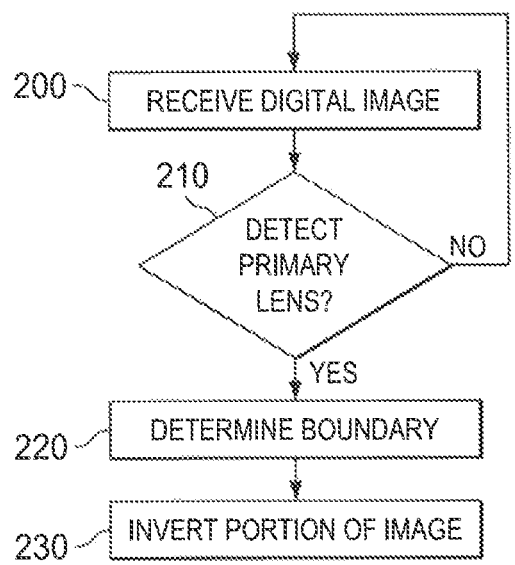
FIG. 4A is a flow-chart of a method for receiving and digitally processing an image of the surgical field in an ophthalmic surgery to detect and correct inversions.
Figure 4B:
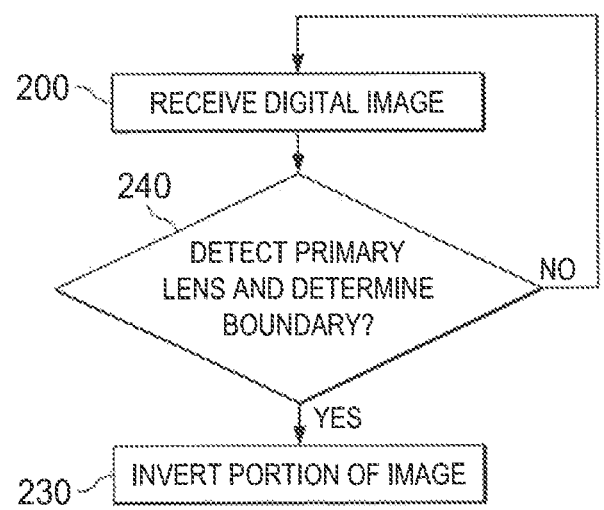
FIG. 4B is a flow-chart of another method for receiving and digitally processing an image of the surgical field in an ophthalmic surgery to detect and correct inversions.

FIGS. 4A and 4B present a flow charts of a method for receiving and digitally processing an image according to the disclosure. In step 200, a digital image, such as that produced by image sensor 130 in system 100, is received by a processing resource. The digital image contains digital information representing light reflected from the surgical field in an ophthalmic surgery performed using surgical instruments, such as instruments 50. The image contains a lens image that has passed through a primary lens, such as primary lens 120, that inverts light beams passing through it to produce an inverted image. The image also contains a peripheral image that has not passed through a primary lens. One of the lens image and peripheral image is inverted and the other is not.

In FIG. 4A, in step 210, the processing resource detects the primary lens using a set of instructions stored in the processing resource or in memory in communication with the processing resource. If a primary lens is detected, then, in step 220, the processing resource determines the boundary of the primary lens within the image. In an alternative method shown in FIG. 4B, in step 240, boundary determination occurs concurrently with detection.

Finally, in step 230, a portion of the image is inverted to create a corrected image, such as corrected image 10. For instance, all of the lens image may be inverted or all of the periphery may be inverted. Alternatively, if instruments or other distinguishable features are also detected, only portions of the image containing these features may be inverted. The correct portion of the image to invert may be pre-set or, for methods used with highly variable systems that may sometimes contain only a primary lens and sometimes also contain an inverter lens, it may be input or determined based upon an identification of the lens or lenses present.

An image may be received in step 200 continuously or at set intervals.

This method and an associated methods to generate the image received in step 200 and display the image created in step 230 may take place in real-time or otherwise with a lag short enough to not hamper the ophthalmic surgery. For instance, the time between light reaching an image sensor, such as image sensor 130, and a corrected image corresponding to that light being displayed, such as on display 150, may be 100 milliseconds or less, 10 milliseconds or less, 4 milliseconds or less, or 1 millisecond or less.

In one method, the processing resource detects an identifier located on or on the lens, typically near its periphery. Typically the identifier is part of the image. The identifier may include a pattern, such as a bar code, not normally found in the eye. The identifier may be placed around the boundary of the primary lens, either continuously or at intervals, allowing the entire boundary to simply be detected by detecting the pattern.

Alternatively, the identifier may be placed in one location or not around the boundary and may identify the type of lens and its dimensions. It may further identify the dimensions and their locations with respect to the identifier. Processing resource 140 may then obtain information about the identified lens from a database and use that information to determine where the boundary is located in the image.

In another method, processing resource 140 may use huge circle detection, for example using the Hough transform, to locate the boundary, which will be substantially circular or elliptical. The set of instructions for huge circle detection may use additional information to exclude other, non-lens circular or elliptical features, such as bubbles. This additional information may include information regarding the type of lens used in the image and its dimensions. The additional information may also include color, which may differ between the exterior and interior of non-lens features, but not for the lens image and the peripheral image. For instance, any bubble-forming liquids in the eye may be dyed to facilitate this method.

In another method, processing resource 140 may use continuity detection to locate the boundary. Continuity detection may locate where features with regular edges, such as instruments, become discontinuous, which is often at the boundary. Continuity detection may be enhanced by using multiple images or continuously received images to detect movement as well. In such methods, changing angles of regular edges may be used to help locate features and places where features become discontinuous.

Any of the above methods used by processing resource 140 may be combined in step 220, in step 230, or in step 240. For instance, once a pattern has been used to identify a lens, huge circle detection may be used to help locate or verify the location of the boundary. In another example, the results of huge circle detection and continuity detection may be combined or used to verify one another.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A system for performing ophthalmic surgery, the system comprising:
    a primary lens through which light reflected from an eye undergoing ophthalmic surgery passes;
    an image sensor that converts the light passed through the primary lens into a lens image and light that has not passed through the primary lens into a peripheral image, wherein the lens image and peripheral image form a digital image;
    a processing resource that identifies a boundary between the lens image and the peripheral image in the digital image and inverts at least a portion of the lens image or at least a portion of the peripheral image to form a corrected image, the processing resource configured to use continuity detection to identify the boundary; and
    a display that displays the corrected image.

2. The system of claim 1, wherein no portion of the corrected image is inverted as compared to the eye.

3. The system of claim 1, wherein less than 10% of the corrected image is inverted as compared to the eye.

4. The system of claim 1, wherein there is at least one surgical instrument in the eye undergoing ophthalmic surgery and no portion of the corrected image containing a surgical instrument is inverted as compared to the surgical instrument.

5. The system of claim 1, wherein there is at least one surgical instrument in the eye undergoing ophthalmic surgery and less than 10% of the corrected image is inverted as compared to the surgical instrument.

6. The system of claim 1, wherein the lens contains an identifier that is detected by the processing resource to identify the boundary.

7. The system of claim 1, wherein the processing resource is further configured to use huge circle detection to identify the boundary.

8. A method of performing ophthalmic surgery comprising:
    placing a primary lens between the eye and an image sensor such that the image sensor receives light reflected from the eye that passes through the lens and light reflected from the eye that does not pass through the lens;
    converting the light received by the image sensor to a digital image containing a lens image converted from light that passes through the lens and a peripheral image converted from light that does not pass through the lens;
    identifying a boundary between the lens image and the peripheral image using a processing resource, the processing resource using continuity detection to identify the boundary;
    inverting at least a portion of the lens image or at least a portion of the peripheral image to form a corrected image; and
    displaying the corrected image.

9. The method of claim 8, wherein no portion of the corrected image is inverted as compared to the eye.

10. The method of claim 8, wherein less than 10% of the corrected image is inverted as compared to the eye.

11. The method of claim 8, further comprising inserting at least one surgical instrument into the eye, wherein no portion of the corrected image containing a surgical instrument is inverted as compared to the surgical instrument.

12. The method of claim 8, further comprising inserting at least one surgical instrument into the eye, wherein less than 10% of the corrected image is inverted as compared to the surgical instrument.

13. The method of claim 8, wherein the primary lens contains an identifier, further comprising detecting the identifier and identifying the boundary using the identifier.

14. The method of claim 13, wherein the identifier is located around the periphery of the lens, such that it corresponds with the boundary.

15. The method of claim 13, further comprising the processing resource using the identifier to obtain information regarding the dimensions of the lens from a database and using the information regarding the dimensions to identify the boundary.

16. The method of claim 8, wherein identifying the boundary comprises the processing resource using huge circle detection.

17. The method of claim 16, further comprising introducing a dye into the eye and using color in huge circle detection to identify the boundary and exclude non-lens circular or elliptical features.

18. The method of claim 8, further comprising the processing resource using two or more of an identifier located on the primary lens or huge circle detection, or continuity detection to identify the boundary.

* * * * *